United States Patent
Jung et al.

(10) Patent No.: US 10,307,382 B2
(45) Date of Patent: Jun. 4, 2019

(54) TRANSDERMAL THERAPEUTIC SYSTEM FOR 5-AMINOLEVULINIC ACID HYDROCHLORIDE

(75) Inventors: Tobias Jung, Efringen-Kirchen (DE); Michael Horstmann, Neuwied (DE); Gerd Hoffmann, Neuwied (DE)

(73) Assignee: Photonamic GmbH & Co. KG, Andernach (DE)

( * ) Notice: Subject to any disclaimer, the term of this patent is extended or adjusted under 35 U.S.C. 154(b) by 621 days.

(21) Appl. No.: 14/240,810

(22) PCT Filed: Aug. 24, 2012

(86) PCT No.: PCT/EP2012/066541
§ 371 (c)(1),
(2), (4) Date: Jun. 18, 2014

(87) PCT Pub. No.: WO2013/030129
PCT Pub. Date: Mar. 7, 2013

(65) Prior Publication Data
US 2014/0323994 A1    Oct. 30, 2014

(30) Foreign Application Priority Data
Aug. 31, 2011  (DE) .................. 10 2011 111 865

(51) Int. Cl.
*A61K 9/70*     (2006.01)
*A61K 31/195*   (2006.01)
*A61K 31/197*   (2006.01)

(52) U.S. Cl.
CPC .......... *A61K 9/7061* (2013.01); *A61K 31/195* (2013.01); *A61K 31/197* (2013.01)

(58) Field of Classification Search
None
See application file for complete search history.

(56) References Cited

U.S. PATENT DOCUMENTS

| 5,976,565 A  | 11/1999 | Fotinos    |
| 7,871,945 B2 | 1/2011  | Berger     |
| 8,465,762 B2 | 6/2013  | Lee et al. |

(Continued)

FOREIGN PATENT DOCUMENTS

| DE | 100 34 673 | 4/2002 |
| EP | 1 210 937  | 5/2002 |

(Continued)

OTHER PUBLICATIONS

As evidenced by the "DURO-TAK and GELVA Transdermal Pressure Sensitive Adhesives", Sep. 2013.*

(Continued)

*Primary Examiner* — Isis A Ghali
(74) *Attorney, Agent, or Firm* — Haug Partners LLP

(57) ABSTRACT

The invention relates to a transdermal therapeutic system, comprising a back layer that is impermeable to an active ingredient, a polymer matrix containing the active ingredient, and a protective layer that can be pulled off, wherein 5-aminolevulinic acid hydrochloride is used as the active ingredient and the basic polymer of the polymer matrix is an adhesive polyacrylate. Said transdermal therapeutic system is suitable for diagnosing and treating preliminary stages of skin cancer, such as actinic keratosis, and oncological skin diseases.

12 Claims, 1 Drawing Sheet

(56) References Cited

U.S. PATENT DOCUMENTS

| | | | | |
|---|---|---|---|---|
| 2002/0058068 A1* | 5/2002 | Houze | ............... | A61K 8/0208 424/487 |
| 2005/0013852 A1 | 1/2005 | Lee et al. | | |
| 2005/0142174 A1 | 6/2005 | Assmus et al. | | |
| 2006/0018956 A1* | 1/2006 | Lee | ............... | A61K 9/7023 424/448 |
| 2006/0182790 A1 | 8/2006 | Mayoral | | |
| 2010/0087768 A1* | 4/2010 | Forlano | ............... | A61K 9/7061 602/48 |
| 2010/0227932 A1 | 9/2010 | Amano et al. | | |

FOREIGN PATENT DOCUMENTS

| | | |
|---|---|---|
| GR | 1002807 | 11/1997 |
| JP | 2000-513347 | 10/2000 |
| JP | 2001-514243 | 9/2001 |
| JP | 2004-503591 | 2/2004 |
| JP | 2004-506005 | 2/2004 |
| JP | 2005-519054 | 6/2005 |
| RU | 2323107 | 10/2007 |
| WO | WO 96/06602 | 3/1996 |
| WO | WO 97/48387 | 12/1997 |
| WO | WO 99/11604 | 3/1999 |
| WO | WO 02/05809 | 1/2002 |
| WO | WO 02/13788 | 2/2002 |
| WO | WO 03/061621 | 7/2003 |
| WO | WO 2006/080199 | 6/2008 |

OTHER PUBLICATIONS

Japanese Office Action corresponding with Japanese Patent Application No. 2014-527607 dated Jan. 26, 2016, 4 pages.

Tim Smits, et al. *New aspects in photodynamic therapy of actinic keratosis* Journal of Photochemistry and Photobiology B: Biology; vol. 96 (2009) pp. 159-169.

* cited by examiner

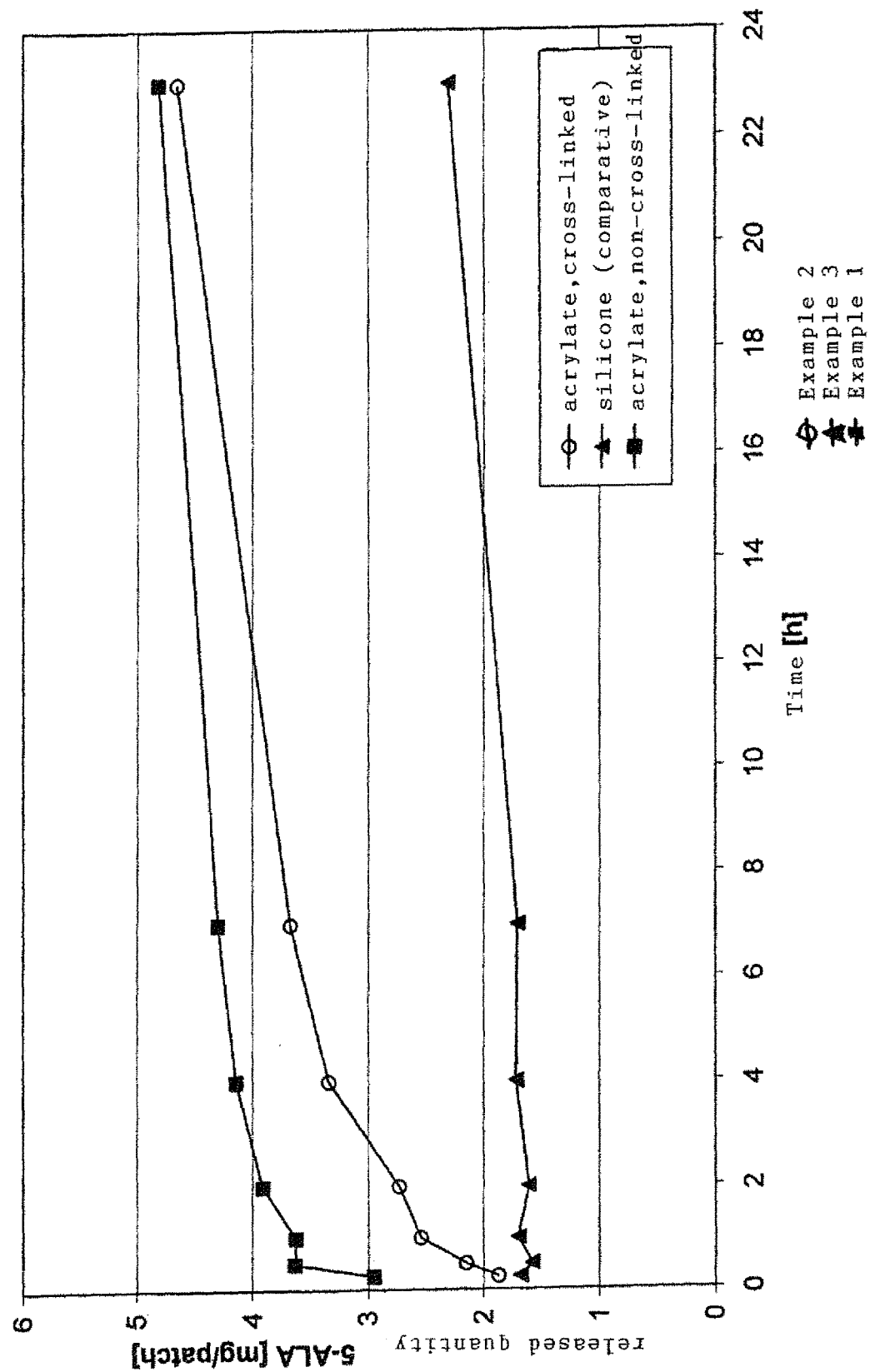

TRANSDERMAL THERAPEUTIC SYSTEM FOR 5-AMINOLEVULINIC ACID HYDROCHLORIDE

The present application claims priority from PCT Patent Application No. PCT/EP2012/066541 filed on Aug. 24, 2012, which claims priority from German Patent Application. No. DE 10 2011 111 865.2 filed on Aug. 31, 2011, the disclosures of which are incorporated herein by reference in their entirety.

FIELD OF THE INVENTION

The present invention relates to a transdermal therapeutic system and a transdermal active ingredient-containing plaster for 5-aminolevulinic acid hydrochloride. It also relates to the use of a system of this type in photodynamic diagnostics and therapy.

It is noted that citation or identification of any document in this application is not an admission that such document is available as prior art to the present invention.

Transdermal therapeutic systems have become widespread nowadays as a form of administration for treating numerous diseases, as they demonstrate certain advantages compared to conventional forms of administration. Thus, transdermal therapeutic systems can increase the therapeutic value of an active ingredient as they ensure a constant dispensing thereof. The advantages of transdermal therapeutic systems are also that, in comparison to ointments or creams, they can be applied to the precise area and therefore at the precise dosage. Furthermore, there is no danger of inadvertently wiping off the ointment and contaminating other locations on the skin.

A transdermal therapeutic system for releasing 5-aminolevulinic acid is known from EP 1 467 706 A1. 5-aminolevulinic acid is selectively absorbed and enriched by tumour tissue, so it only leads to an increased porphyrin formation and concentration there, while the healthy tissue remains substantially uninfluenced. The effect of the 5-aminolevulinic acid is based on the stimulation of the body's own porphyrin formation. As the porphyrin strongly fluoresces upon irradiation, the 5-aminolevulinic acid or porphyrin enrichment can be used in diseased tissue to diagnose precancerous and cancerous lesions and for the protodynamic therapy thereof. A similar system is also known from EP 1 303 267 A1. The two systems have the drawback that the 5-aminolevulinic acid permeates through human skin only comparatively poorly.

Actinic keratosis is designated an early form of white skin cancer, as the latter in 10% of cases can develop within a period of 10 years into a squamous cell carcinoma of the skin (spinalioma). It is chronic damage to the horny epidermis caused by the intensive action of sunlight (UV radiation) over many years. An important treatment method for actinic keratosis is so-called photodynamic therapy. An active ingredient is firstly applied here to the affected skin region and specific light-sensitive substances, the so-called porphyrins, increasingly form in the diseased skin cells. As a result, the cells are sensitised to the subsequent treatment with light and reactive oxygen is produced (photodynamic effect), which ultimately leads to the death of the corresponding cells. Good cosmetic results can generally be achieved using the photodynamic therapy. The photodynamic therapy can furthermore be repeated virtually as often as desired if the actinic keratosis occurs again. Apart from the therapeutic effect, photodynamic therapy also offers a diagnostic use. Using special light, the regions affected by actinic keratosis and pretreated by corresponding substances can be made visible in a targeted manner. It is thus possible to recognise the actinic keratosis early and to precisely determine the size of the locations affected (photodynamic diagnostics).

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

It is further noted that the invention does not intend to encompass within the scope of the invention any previously disclosed product, process of making the product or method of using the product, which meets the written description and enablement requirements of the USPTO (35 U.S.C. 112, first paragraph) or the EPO (Article 83 of the EPC), such that applicant(s) reserve the right to disclaim, and hereby disclose a disclaimer of, any previously described product, method of making the product, or process of using the product.

SUMMARY OF THE INVENTION

The aim of the present invention is to provide a transdermal therapeutic system, which as quickly as possible releases an adequate quantity of a substance into precancerous and cancerous lesions in order to then carry out the photodynamic therapy by means of irradiation. The transdermal therapeutic system should be well tolerated by the skin, be flexible and adequately sticky, even on regions that are less well accessible, such as the nasal bone or the outer ear. Furthermore, the transdermal therapeutic system should be stable, visually unobtrusive, easy to apply and remove again.

The above aim is addressed by a transdermal therapeutic system or a transdermal active ingredient-containing plaster, which comprises a back layer that is impermeable to an active ingredient, an active ingredient-containing polymer matrix and a protective layer that can be pulled off, and characterised in that 5-aminolevulinic acid hydrochloride is used as the active ingredient and in that the basic polymer of the polymer matrix is an adhesive polyacrylate.

DETAILED DESCRIPTION OF EMBODIMENTS

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

The transdermal therapeutic system according to the invention with 5-aminolevulinic acid hydrochloride as the active ingredient and an adhesive polyacrylate as the basic polymer of the polymer matrix is in a position to absorb adequately large quantities of the suspended pharmaceutical agent, i.e. of the 5-aminolevulinic acid hydrochloride. There is good compatibility between the adhesive polyacrylate used and the 5-aminolevulinic acid hydrochloride. The release rate of the 5-aminolevulinic acid hydrochloride during the application period is extraordinarily high. Furthermore, the transdermal therapeutic system according to the invention adheres adequately to the skin but does not irritate it. The transdermal therapeutic system according to the invention can easily be applied, especially also to small skin regions, such as the forehead, the outer ear or the nose.

According to a preferred embodiment, the transdermal therapeutic system according to the invention is characterised in that it is capable, within about four hours, preferably within about an hour and especially preferably within about thirty minutes, of releasing a quantity of at least 3 mg 5-aminolevulinic acid hydrochloride (measured as 5-aminolevulinic acid with the so-called "paddle over disc" method, as described in European Pharmacopoeia 6.0, 2.9.4 "dissolution test for transdermal patches", 01/2008: 20904; see also Example 4).

The transdermal therapeutic system according to the invention is preferably a monolithic active ingredient-in-adhesive system (monolithic drug-in-adhesive system). 5-aminolevulinic acid hydrochloride is suspended or dispersed directly in the polymer matrix here. The polymer matrix carries out the three functions of the active ingredient reservoir, the control element and the adhesive layer in this case. A system of this type consists only of a back layer that is impermeable to an active ingredient, an active ingredient-containing polymer matrix and a protective layer that can be pulled off. The polymer matrix influences the adhesion to the skin, the storage of the 5-aminolevulinic acid hydrochloride and its release. A system of this type leads to a plurality of advantages during the release of hydrophilic substances, such as 5-aminolevulinic acid hydrochloride. Thus, further hydrophilic matrix materials can be avoided, so the microbiological stability is improved. The stability of the active ingredient is also increased as it is chemically inactivated. It is furthermore possible to control the release of the active ingredient by means of the particle size.

The back layer that is impermeable to the active ingredient is preferably inert and as flexible as possible, so the transdermal therapeutic system can also be applied to irregular skin regions. Any suitable material, such as, for example, polyethylene terephthalate, polyethylene, polybutylene, polyurethane, polyester, etc., can be used for the back layer. The back layer that is impermeable to an active ingredient is preferably an optionally aluminised polyester film, especially preferably a laminate made of pigmented polyethylene with aluminium vapour-coated polyester, which (provide) protection against light irradiation and therefore prevent photosensitisation before the actual photodynamic therapy.

The protective layer that can be pulled off can be produced from various materials, such as, for example, polyethylene terephthalate, polyethylene or polypropylene and is specially treated on the side in contact with the active ingredient-containing polymer matrix in order to make it as easy as possible to remove therefrom. The protective layer that can be pulled off is advantageously based on a polyethylene terephthalate layer.

In a preferred embodiment, the active ingredient 5-aminolevulinic acid hydrochloride is present as a crystalline 5-aminolevulinic acid hydrochloride. This has the advantage that the solubility of the active ingredient in the matrix does not have to be adjusted. Furthermore, an over-saturation and a constant diffusion pressure are thereby achieved.

In a preferred embodiment, about 50% of the crystals or particles of the crystalline 5-aminolevulinic acid hydrochloride are greater than the layer thickness of the polymer matrix. The active ingredient projects, so to speak, from the matrix, which has the advantage that on contact with the skin, especially with sweat, the projecting crystals very quickly dissolve and can therefore be easily and quickly transdermally absorbed.

More than 99.9% of the crystals of the crystalline 5-aminolevulinic acid hydrochloride are preferably smaller than about 250 µm. Although as the crystal size becomes larger, the epidermal flow increases, crystals that are too large, i.e. crystal sizes above about 250 µm, lead to clumping and streak formation.

On the other hand, it is preferred for the quantity of crystals, which are smaller than 90 µm, to make up at most 50%, and the quantity of crystals, which are smaller than 50 µm, to make up at most 25%, of the active ingredient mass, as this ensures a high active ingredient flow.

A transdermal therapeutic system with 5-aminolevulinic acid hydrochloride crystals of a particle size of 90 to 160 µm exhibits a clearly improved transepidermal flow compared with a system with particles having a particle size of less than 90 µm. This is probably because more active ingredient is released and is therefore available for the permeation. Particle sizes in the range from 90 to 160 µm are therefore especially preferred.

The polymer matrix of the transdermal therapeutic system according to the invention preferably contains less than 30% by weight, preferably less than 20% by weight and especially preferably less than 5% by weight of plasticiser, for example citric acid esters, such as acetyl tributyl citrate, in relation to polyacrylate. The plasticiser content in the transdermal therapeutic system according to the invention is quite especially preferably below 5000 ppm.

So-called enhancers or permeation promoters can also preferably be dispensed with.

The adhesive polyacrylate can be obtained with and advantageously without cross-linking agents (cross-linkers), such as, for example, aluminium acetylacetonate, polybutyl titanate or t-amyl peroxy pyrolate, etc.

The adhesive polyacrylate preferably has acid functionalities (carboxyl groups), as they are advantageous in relation to the adhesion. These are especially important when the crystals of the crystalline 5-aminolevulinic acid hydrochloride are larger than the layer thickness of the polymer matrix as whole-area contact between the transdermal therapeutic system and the skin is not then ensured. The adhesive polyacrylate with acid functionalities can, for example, be obtained by polymerisation of a monomer mixture containing an unsaturated carboxylic acid, such as, for example, acrylic acid, methacrylic acid or maleic acid.

The monomer mixtures used to produce the adhesive polyacrylates can also contain acrylic acid derivatives with epoxy groups, such as, for example, glycidyl (meth)acrylate.

The polyacrylate is preferably based on acrylic esters, such as, for example, 2-ethylhexyl acrylate. This is preferably used in a quantity of more than 50% by weight, especially more than 60% by weight and especially preferably in a quantity of more than 70% by weight, based on polyacrylate.

The viscosity of the polyacrylate is preferably in the range from 500 to 25,000, especially preferably in the range from 1,000 to 20,000 and quite especially preferably in the range from 1,500 to 12,000 mPa·s at 25° C.

In a preferred embodiment, the adhesive polyacrylate is polyacrylate based on acrylic acid, butyl acrylate, 2-ethylhexyl acrylate and vinyl acetate, based on 2-ethylhexyl acrylate, 2-hydroxyethyl acrylate and vinyl acetate, based on acrylic acid, 2-ethylhexyl acrylate and methyl acrylate, based on acrylic acid, 2-ethylhexyl acrylate and vinyl acetate, based on 2-ethylhexyl acrylate, 2-hydroxyethyl acrylate and methyl acrylate, based on 2-ethylhexyl acrylate, 2-hydroxyethyl acrylate and methyl acrylate, based on acrylic acid, butyl acrylate, 2-ethylhexyl acrylate, vinyl acetate, 2-hydroxyethyl acrylate and methyl methacrylate, based on acrylic acid, butyl acrylate, 2-ethylhexyl acrylate, vinyl acetate, t-octylacrylamide and vinyl acetate and based on 2-ethylhexyl acrylate and vinyl acetate.

Adhesive acrylates based on acrylic acid, butyl acrylate, 2-ethylhexyl acrylate and vinyl acetate and adhesive polyacrylates based on acrylic acid, 2-ethylhexyl acrylate and methyl acrylate, the latter supplying the best results, are especially preferred.

The adhesive polyacrylate mentioned first based on acrylic acid, butyl acrylate, 2-ethylhexyl acrylate and vinyl acetate is preferably produced from a monomer mixture, which contains 1 to 10% by weight, preferably 3 to 7% by weight and especially preferably about 5% by weight acrylic acid, 5 to 25% by weight, preferably 10 to 20% by weight, and especially preferably about 15% by weight butyl acrylate, 60 to 80% by weight, preferably 70 to 78% by weight, and especially preferably about 75% by weight 2-ethylhexyl acrylate and 1 to 10% by weight, preferably 2 to 8% by weight, and especially preferably about 5% by weight vinyl acetate.

The adhesive polyacrylate based on acrylic acid, 2-ethylhexyl acrylate and methyl acrylate are preferably produced from a monomer mixture, which contains 1 to 10% by weight, preferably 2 to 8% by weight, and especially preferably about 5.7% by weight acrylic acid, 50 to 70% by weight, preferably 55 to 65% by weight, and especially preferably about 62.2% by weight 2-ethylhexyl acrylate and 20 to 40% by weight, preferably 30 to 35% by weight, and especially preferably about 32% by weight methyl acrylate. In the case of the latter, small quantities of glycidyl methacrylate, for example less than 1% by weight, preferably less than 0.05% by weight, and especially preferably about 0.03% by weight, glycidyl methacrylate can also be present.

In a preferred embodiment, the polymer matrix of the transdermal therapeutic system according to the invention contains more than 10% by weight and especially preferably more than 20% by weight 5-aminolevulinic acid hydrochloride. It was experimentally established that the release of the 5-aminolevulinic acid hydrochloride increases within the first hour, by increasing the active ingredient quantity from 20% by weight to 30% by weight, by about a factor of 6.

On the other hand quantities of 5-aminolevulinic acid hydrochloride that are too large lead to a deterioration in the ability to adhere to the skin and to problems in the coating. It is therefore preferred if less than 35% by weight and especially less than 30% by weight 5-aminolevulinic acid hydrochloride is present. The range between 25 and 30% by weight is optimal.

The quantity of the polyacrylate used in the transdermal therapeutic system according to the invention is preferably more than 60% by weight and especially preferably more than 70% by weight.

In a preferred embodiment, the transdermal therapeutic system is a monolithic active ingredient-in-adhesive system, more than 99.9% of the crystals of the crystalline 5-aminolevulinic acid hydrochloride are smaller than 250 µm, the adhesive polyacrylate is based on acrylic acid, butyl acrylate, 2-ethylhexyl acrylate and vinyl acetate and especially preferably on acrylic acid, 2-ethylhexyl acrylate and methyl acrylate, and the polymer matrix contains 25 to 30% by weight, preferably about 28% by weight, 5-aminolevulinic acid hydrochloride and 70 or more % by weight, preferably about 72% by weight, polyacrylate. A system of this type exhibits a very rapid release of a large quantity of active ingredient and the processability is excellent.

The transdermal therapeutic system according to the invention is produced in a known manner. An active ingredient-containing adhesive mass based on an adhesive polyacrylate is firstly produced. Ethanol, ethyl acetate, heptane, hexane, isopropyl alcohol, methanol, toluene, 2,4-pentandiene and mixtures thereof are preferably possible solvents. Ethyl acetate and hexane are especially preferred. Conventional coating, drying and laminating methods and cutting follow. The solvent is almost completely removed during the drying process. Perforation and packaging finally follow.

The present invention also relates to the use of the transdermal therapeutic system according to the invention for the diagnosis and therapy of preliminary skin cancer stages, such as actinic keratosis, and of skin cancer and oncological skin diseases. The external application of the transdermal therapeutic system leads to the penetration and enrichment of the active ingredient in the diseased tissue. 5-aminolevulinic acid hydrochloride is an endogenous compound and a precursor substance in the biosynthesis of porphyrins, which are constituents, for example, of the haemoglobin and the cytochrome cycle. 5-aminolevulinic acid hydrochloride is converted into the actual photosensitiser, the protoporphyrin IX (PPIX). After the enrichment, an irradiation takes place with adequate light, for example with light of various wavelengths, such as, for example, 408 mm, 506 mm, 532 mm, 580 mm and 635 mm. In this case, reactive oxygen compounds are produced, which make the target tissue visible during the diagnosis or lead to an apoptosis and necrosis thereof during the therapy.

The present invention also relates to a transdermal therapeutic system, as described above, as a therapeutic agent.

Furthermore, the present invention relates to a transdermal therapeutic system, as described above, for treating preliminary skin cancer stages, such as, for example, actinic keratosis, and oncological skin diseases. The transdermal therapeutic system is preferably used to treat actinic keratosis.

OPERATIVE EXAMPLES

The subject matter of the present invention is elucidated in more detail below, using examples, without any intention that the subject matter of the invention should be confined to these exemplary embodiments.

Example 1

The transdermal therapeutic system produced contains the following constituents:

| | | % (% by weight/% by weight) | mg/Plaster |
|---|---|---|---|
| Active ingredient: | 5-aminolevulinic acid hydrochloride | 19.7 | 10.2 |
| Polymer [a]: | DURO-TAK 387-2353 | 49.6 | 25.8 |
| Back layer: | 3M ScotchPak 1109 | 30.7 | 16.0 |

-continued

| | % (% by weight/% by weight) | mg/Plaster |
|---|---|---|
| Protective layer: polyethylene terephthalate layer siliconised on one side (75 μm) | [b)] | 59.0 [c)] |

[a)] in ethyl acetate and hexane, which are both virtually completely removed during the drying process
[b)] is removed before application
[c)] estimated In relation to the polymer matrix, 28% by weight 5-aminolevulinic acid hydrochloride and 72% by weight DURO-TAK 387-2353 (polyacrylate without cross-linking agent) are accordingly present.

Example 2

The composition of this example corresponds to Example 1, except that instead of DURO-TAK 387-2353, the same quantity of DURO-TAK 387-2052 (polyacrylate with cross-linking agent) was used.

Comparative Example 3

The composition of this example corresponds to Example 1, except that instead of DURO-TAK 387-2353, the same quantity of Bio-PSA 4301 (a silicone polymer) was used.

Example 4

The release rate was measured using the so-called "paddle over disc" method, as described in European Pharmacopoeia 6.0, 2.9.4. "dissolution test for transdermal patches", 0112008: 20904, under the following conditions:
  Apparatus used: paddle over disc
  Release medium: citrate buffer pH 3.0
  Volume of the release medium: 300 ml
  Temperature: 32° C.±0.5° C.
  Rotation frequency: 50 min$^{-1}$
  Sample removal time: 0.5 h, 2 h and 7 h
  Sample volume: 10.0 ml
  The results are shown in FIG. 1.

The release rate of a transdermal therapeutic system according to Example 1 is higher than that according to Example 2. Both Example 1 and Example 2 exhibit a clearly faster release compared to comparative Example 3. Furthermore, the stability of the 5-aminolevulinic acid hydrochloride according to Example 1 after one and three months is higher than that of the 5-aminolevulinic acid hydrochloride according to Example 2, which is degraded more quickly.

BRIEF DESCRIPTION OF THE DRAWING

The invention is illustrated hereinafter by a drawing and the above working examples, the drawings and working examples serving merely for illustration but not restricting the invention.

FIG. 1 is a graph showing released quantity 5-ALA [mg/patch] versus time [h] for Examples 1, 2, and 3. Example 1 is acrylate (non cross-linked), Example 2 is acrylate (cross-linked), and Example 3 is silicone (comparative).

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

The invention claimed is:

1. A transdermal therapeutic system, comprising:
  a back layer that is impermeable to an active ingredient;
  an active ingredient-containing polymer matrix; and
  a protective layer that can be pulled off;
  wherein the polymer matrix consists of:
    about 28% by weight of crystalline 5-aminolevulinic acid hydrochloride as the active ingredient; and
    about 72% by weight of a non-crosslinked polyacrylate adhesive based on acrylic acid, 2-ethylhexyl acrylate, and methyl acrylate;
  wherein the transdermal therapeutic system is a monolithic active ingredient-in-adhesive system; and
  wherein the transdermal therapeutic system releases within about four hours, an amount of at least 3 mg 5-aminolevulinic acid hydrochloride.

2. The transdermal therapeutic system according to claim 1;
  wherein 50% of the crystals of the crystalline 5-aminolevulinic acid hydrochloride are larger than the layer thickness of the polymer matrix.

3. The transdermal therapeutic system according to claim 1;
  wherein more than 99.9% of the crystals of the crystalline 5-aminolevulinic acid hydrochloride are smaller than about 250 μm.

4. The transdermal therapeutic system according to claim 1;
  wherein the polyacrylate has acid functionalities.

5. A method comprising:
  utilizing the transdermal therapeutic system according to claim 1 as a therapeutic agent.

6. A method comprising:
  utilizing the transdermal therapeutic system according to claim 1 for treating preliminary skin cancer stages.

7. A method comprising:
  utilizing the transdermal therapeutic system according to claim 1 for diagnosing and treating preliminary skin cancer stages.

8. The transdermal therapeutic system according to claim 3;
  wherein more than 99.9% of the crystals of the crystalline 5-aminolevulinic acid hydrochloride have a particle size of 90 to 160 μm.

9. The method according to claim 6;
  wherein the skin cancer is selected from the group consisting of actinic keratosis and oncological skin diseases.

10. The method according to claim 7;
  wherein the skin cancer is selected from the group consisting of actinic keratosis and oncological skin diseases.

11. The transdermal therapeutic system according to claim 1;
  wherein the transdermal therapeutic system releases at least 35% of the 5-aminolevulinic acid hydrochloride within thirty minutes.

12. The transdermal therapeutic system according to claim 1;
  wherein the polymer matrix consists of:

28% by weight of crystalline 5-aminolevulinic acid hydrochloride as the active ingredient; and 72% by weight of a non-crosslinked polyacrylate adhesive based on acrylic acid, 2-ethylhexyl acrylate, and methyl acrylate.

\* \* \* \* \*

UNITED STATES PATENT AND TRADEMARK OFFICE
CERTIFICATE OF CORRECTION

PATENT NO. : 10,307,382 B2
APPLICATION NO. : 14/240810
DATED : June 4, 2019
INVENTOR(S) : Jung et al.

Page 1 of 1

It is certified that error appears in the above-identified patent and that said Letters Patent is hereby corrected as shown below:

On the Title Page

Item (73):
Delete "Photonamic GmbH & Co. KG, Andernach (DE)"
Insert --LTS Lohmann Therapie-Systeme AG, Andernach (DE);
Photonamic GmbH & Co. KG, Pinneberg (DE)--

Signed and Sealed this
Seventh Day of April, 2020

Andrei Iancu
*Director of the United States Patent and Trademark Office*